United States Patent [19]

DeBusk et al.

[11] Patent Number: 4,948,651
[45] Date of Patent: Aug. 14, 1990

[54] BURN SHEET

[75] Inventors: Autry O. V. DeBusk; Charles A. Lee, both of Knoxville, Tenn.

[73] Assignee: DeRoyal Industries, Inc., Powell, Tenn.

[21] Appl. No.: 372,870

[22] Filed: Jun. 27, 1989

[51] Int. Cl.⁵ .............................................. B32B 3/10
[52] U.S. Cl. .................................. 422/110; 128/155; 428/109; 428/226; 428/229; 428/247
[58] Field of Search ............... 428/109, 110, 131, 137, 428/138, 247, 255, 226, 229; 128/155

[56] References Cited

U.S. PATENT DOCUMENTS

| | | | |
|---|---|---|---|
| 2,902,395 | 9/1959 | Hirschy et al. | 428/109 |
| 3,597,299 | 8/1971 | Thomas et al. | 428/109 |
| 3,622,423 | 11/1971 | Hadley | 428/294 |
| 3,716,132 | 2/1973 | Lewjckyj | 428/105 |
| 4,001,472 | 1/1977 | Thomas et al. | 428/109 |

Primary Examiner—James J. Bell
Attorney, Agent, or Firm—Luedeka, Hodges & Neely

[57] ABSTRACT

A burn sheet comprising a plurality of layers laminated one to another and including a liquid-permeable top layer, a liquid-absorbent layer and a strength-imparting scrim layer. The scrim layer comprises an open pattern of crossing multifilamentary yarns bonded on one another at their crossings. The scrim is flattened prior to its incorporation into the burn sheet laminate so that cut ends of the scrim yarn monofilaments yield to the touch and the sheet is rendered conformable, and telegraphing of the scrim to the surface of the sheet is minimized. The sheet is suitable for use as a transfer sheet as well as for a burn sheet.

11 Claims, 1 Drawing Sheet

BURN SHEET

This invention relates to sheet products which serve primarily to support and protect a burn patient. Such sheets provide for absorption of wound exudate and as a protective covering between the patient and a bed, for example.

Burn patients, especially those patients which have suffered burns over major portions of their body, are treated in accordance with different protocols. One such protocol provides that the burned area be maintained dry during the natural healing process. Another such protocol provides that there be applied to the burned area a lotion or cream, usually medicated, so that the burned areas are kept semi-isolated from the air during the natural healing process. Either protocol is intended to maximize the growth of new tissue while minimizing the development of scar tissue. This is accomplished by encouraging the natural healing process. In the course of the natural healing process for burn wounds the body generates relatively large volumes of exudate and eventually regrowth of tissue in the affected areas. In all known protocols for the treatment of burn wounds, it is the practice to periodically debride the patient to remove eschar tissue and thereby encourage the growth of natural new skin tissue, as opposed to eschar tissue, the latter tending to contract the skin and or muscle tissue in the burn area and possibly limit the mobility of a body member.

Obviously, burn wounds are most painful. Thus, movement of the patient frequently is restricted to only those movements necessary in the care of the patient and even these movements are carried out with great care to not disturb the healing wounds nor inflict pain upon the patient. Further, in all protocols for treating burn wounds, there is always provision made for minimizing the exposure of the patient to the possibility of infection. For these and other reasons, great care is taken in transferring a burn patient between locations within the treatment facility and even in the desired rotation of the patient's position in a bed for purposes of comfort and promotion of healing. In many instances, it is desirable that the patient not be touched during movement.

In the prior art, it has been the practice to place a burn patient upon a sheet which preferably absorbs exudate from the burn wounds and which preferably also protects against the exudate contaminating the customary bed linens. Most importantly, the sheet should encourage, not discourage, the natural healing process. Thus, the sheet should not adhere to the patient and especially should not penetrate the wound area such that eschar tissue tends to attach to the sheet.

Burn sheets are at times referred to as "transfer sheets" in that they are also used to transfer the patient, while on the sheet, from location to location. Such transfer is accomplished as by several attendants grasping opposite sides of the sheet and lifting the sheet and patient simultaneously. One of the problems associated with such prior art sheets is the failure of the sheet to function effectively as an exudate-absorbing member and still be strong enough to enable its side edges to be grasped and permit its use as a transfer sheet. The importance of not dropping a burn patient during transfer is obvious.

Further, because of the sensitive nature of the contact between a burn wound area and a burn sheet, such burn sheet must not present any rough or abrasive area which may contact the patient. This includes the side edges of the burn sheet as well as the flat surfaces thereof. For example, for the comfort of the patient, the burn sheet cannot exhibit ridges or protrusions from its flat supporting surface such as would make the surface uncomfortable to lay upon. The sensitivity of the exposed nerve endings in burn wounds requires a greater than normal smooth and comfortable supporting surface for the patient. As noted, it is important also that the burn sheet not adhere to the patient, and especially it should not adhere to a wound area.

In accordance with the present invention, there is provided a burn sheet that functions effectively both as a burn sheet and as a transfer sheet. In the present product, the inventors combine multiple layers of differing materials in a manner that provides excellent absorptivity of exudate, strength for patient transfer, and patient comfort. Such burn sheet comprises a top layer which presents a smooth, non-adhering surface for contacting the patient. This layer is overlaid, and preferably bonded, to a layer of highly absorbent material. Exudate from the burn wound passes through the top layer and is absorbed by the second layer. These two layers are overlaid upon a scrim, which in turn is overlaid upon a liquid impermeable layer so that the scrim is captured between the absorbent layer and the impermeable (i.e., bottom) layer. All layers preferably are bonded to their respective adjacent layer(s). Importantly, the scrim employed in the present invention is formed from multifilamentary yarns, which are flattened, as by calendaring, and with the individual monofilaments of each yarn being bonded to one another and to the monofilaments of crossing yarns at their junctures.

Accordingly, it is an object of the present invention to provide a burn sheet having good absorptivity for wound exudate and strength for allowing the sheet to be used as a transfer sheet. It is another object to provide a burn sheet having a reinforcing scrim incorporated therein and which does not detract deleteriously from the comfort of a patient disposed thereon. It is another object of the present invention to provide a burn sheet which provides an enhanced patient-contact surface that enhances the normal healing process for burn wounds. These and other objects of the invention will be recognized from the description provided herein including the drawings in which:

BRIEF DESCRIPTION OF THE DRAWING

Referring now to FIG. 1, in one embodiment of a burn sheet 10 in accordance with the present invention, such sheet comprises a top layer 12 which is intended to be in direct contact with a burn patient disposed thereon. This top layer 12 preferably is of a synthetic material which exhibits a smooth and relatively continuous outer surface 14 which does not penetrate into the burn wound, but rather defines a conformable barrier between the wound and the remainder of the sheet. This layer is permeable to wound exudate and permits the flow of exudate through the thickness of the layer but is not so open as to permit the formation of eschar tissue in the open spaces therein, hence the layer does not adhere to the wound. To this end, the layer may be of a material whose permeability is a function of the formation of the web, as in spun-bonded or melt-blown webs, or the web may be formed as a solid web and thereafter perforated. In a preferred embodiment the top layer 12 is a perforated plastic web. One suitable web is Delnet, a high density polyethylene web that has been perforated to make the web liquid-permeable, which is manufactured by Applied Extrusion Technologies, Inc. of Middletown, Del. The preferred top layer 12 has a thickness of between about 3.8 to 4.8 mils and a Frazier air permeability of about 700 ft.$^3$/ min/ft.$^2$.

The top layer 12 is overlaid upon an absorbent layer 16, which in a preferred embodiment is a layer of defiberized cellulose, e.g. wood fluff, having a basis weight of between about 50 and 125 g/m$^2$, a caliper of between about 0.0005 and 0.003 inch, and a water absorbency of not less than about 0.5 sec/ml. The fibers of the preferred absorbent fluff layer are air laid and bonded one to another as by an adhesive such as ethylene vinyl acetate so as to render the web self-sustaining for processing through conventional lamination equipment. The fluff may be formed as a single ply, but preferably is of multiple plies which are compressed to form a unitary layer.

The bottom layer 18 of the present burn sheet may be of the same material as the top layer 12 in the event it is desired that the sheet be permeable through its full thickness. In a preferred sheet the bottom layer 18 is impermeable to liquids so as to prevent strike-through of exudate, etc. to bed linens or the like. Thus, the preferred web for use as the bottom layer is a polyethylene web having a thickness of about 0.0015", such as is available from Clopay Corporation of Cincinnati, Ohio. The preferred web is embossed to enhance its texture.

Figure 3:
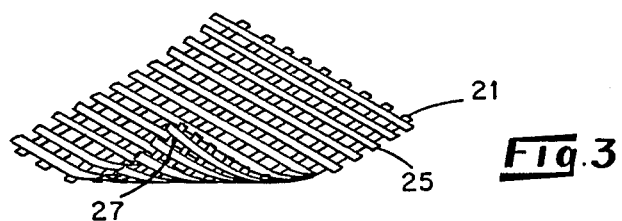
FIG. 3 is a fragmentary representation of one embodiment of a scrim as employed in the present invention.
Figure 4:
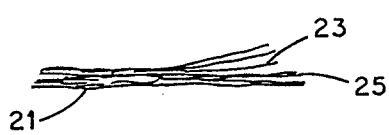
FIG. 4 is a representation of a multifilamentary yarn employed in one embodiment of a scrim as used in the present invention and showing certain of the monofilaments thereof.

Interposed between the absorbent layer 16 and the bottom layer 18 there is provided a scrim 20. One embodiment of suitable scrim is depicted in FIG. 3. The principal function of this scrim layer is to impart strength to the present burn sheet, hence the yarns thereof necessarily are of relatively large sizes. Due partly to such large size (i.e. denier) of these yarns, the presence of the scrim in the laminate tends to be exhibited by the development of ridges or prominences on that surface of the sheet which is in contact with the patient, (i.e. telegraphing of the scrim) thereby making the sheet uncomfortable. Further, when the yarns employed in the scrim are monofilamentary and the laminated material is cut to size for use as a sheet, the cut ends of the yarns of the scrim present very sharp edges that at the best are uncomfortable to the patient and the attendants who apply, adjust and/or remove the sheet, and often can actually pierce the skin. Such sharp edges also tend to gouge into open wounds with resultant irritation and disruption of the normal healing process. In accordance with the present invention, it has been discovered that if a scrim comprising multifilamentary yarns 21, made up of large numbers of relatively small monofilamentary yarns 23, and flattened as by calendaring prior to incorporation into the present sheet, when laminated into a burn sheet and cut to size, produces cut ends 25 of the flattened yarns of the scrim which yield when contacted by users of the sheet such as attendants or the patient and do not exhibit sharp edges as do the cut ends of rounded yarns, especially monofilamentary yarns. Thus, the preferred scrim comprises a relatively heavy-weight, open multifilamentary scrim 20 which has been passed through a calendaring operation that serves to flatten the yarns 21 of the scrim. With a scrim which has been initially formed by bonding the overlaid yarns at their crossings 27 with a heat rebondable adhesive, the preferred calendaring is by means of heated calendaring rolls. As noted the calendaring takes place prior to incorporation of the scrim into the burn sheet. In a preferred calendaring operation, the yarns of the scrim are flattened such that their flat width is slightly less than twice their diameter when in their unflattended condition. By this means, the scrim does not telegraph its presence in the burn sheet when the several layers of the burn sheet are passed through a laminator. This flattening operation serves to "fan" out the monofilaments 23 that make up a yarn 21 thereby rendering the otherwise stiff yarn flexible and contributing to the desired drape and conformability of the burn sheet. This fanning out at the ends of the yarns further provides for yieldable ends of the monofilamentary when cut, hence elimination of the objectionable sharp cut ends of monofilamentary yarns.

The flattened thickness of the scrim yarns preferably is between about 0.005" and about 0.015". The scrim has a yarn count of between about 2 and about 12 ends/inch in the machine direction and a like or similar yarn count in the cross direction. One suitable scrim includes 4 yarns per inch in the machine direction and 3 yarns per inch in the cross direction. Each yarn has a tensile strength of about 15 pli, is of about 1,000 denier, and preferably comprises at least about 192 individual monofilaments. The yarns preferably are overlaid in a nonwoven open pattern and bonded at their crossing points to one another as by means of a heat rebondable adhesive such as an acrylic latex. The weave may be a square weave or any of other open weaves. The preferred scrim has an elongation that does not exceed about 30%, and preferably has an elongation of less that about 25% in either of its machine or cross directions. Yarns of about 1000 denier present in a weave and yarn count appropriate to develop a basis weight of between about 1 and about 2 oz/yd$^2$ are preferred. An open polyester scrim mesh coated with a polyvinyl chloride binder such as that available from Bayex Inc. of Albion, N.Y., and sold under the trademark Bayex has been found most suitable.

In the preferred burn sheet, the scrim layer 20 is disposed between the absorbent layer 16 and the bottom layer 18. By this means, the scrim provides maximum support to the relatively weak absorbent layer and top layer when the burn sheet is used as a transfer sheet. Preferably, the laminated burn sheet has a tensile strength sufficient to permit the lifting and transfer of a patient disposed on the sheet by attendants grasping the side edges 40 and 42 of the sheet for lifting. Thus, tensile strengths of between about 45 and about 60 pli are preferred. Also, the absorbent sheet, being relatively thick, provides cushioning between the patient and the scrim.

Figure 1:
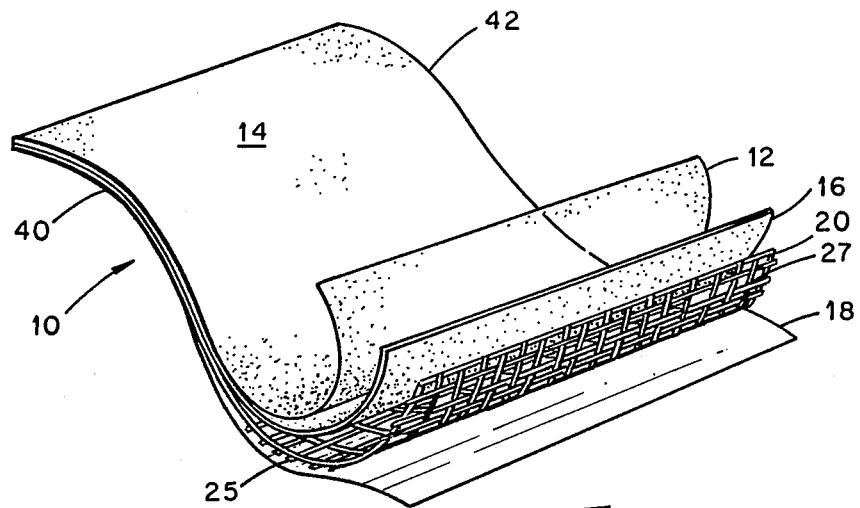
FIG. 1 is a schematic representation of one embodiment of a burn sheet in accordance with the present invention and showing a portion of the multiple layers thereof separated for purposes of illustration, and, FIG. 2 is a schematic diagram of a laminating apparatus for use in the manufacture of the present burn sheet.
Figure 2:
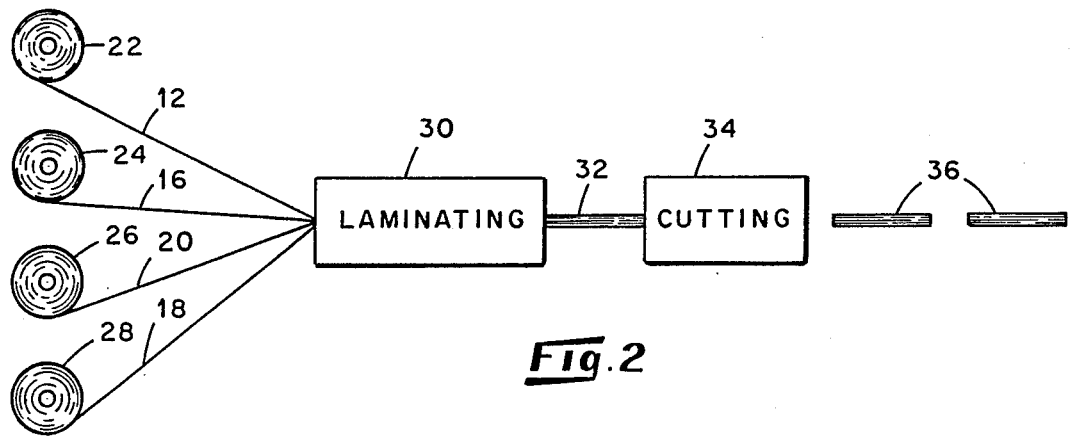

The several layers of the present burn sheet are laminated into a composite sheet employing conventional laminating procedures and equipment. For example, as depicted in FIG. 2, the top layer 12, absorbent layer 16, scrim layer 20 and the bottom layer 18 may originate from parent rolls 22, 24, 26, and 28 of the same and be fed forwardly into a laminator 30. At the laminator, an adhesive such as an acrylic polymer emulsion, is applied to the mating surfaces of the layers and the same are then guided into overlaying relationship and passed through a set of pressure rolls (not shown). The laminated product 32 is next passed to a cutting station 34 where the laminate is cut into the desired sheet sizes. The cut sheets 36 are collected for packaging and shipment. Importantly, in the application of adhesive to that surface of the top layer 12 which is ultimately bonded to the absorbent layer 16 it is important that the adhesive be applied in a manner such that the adhesive does not materially block the permeability of the top layer 12. This may be accomplished by applying the adhesive in a pattern, such as an open diamond pattern. Other techniques for accomplishing the desired result will be recognized by one skilled in the art. As desired, there may be employed a multi-pass lamination procedure in which two or three of the layers are initially overlaid with a further layer. For example, the bottom layer, the scrim, and the absorbent layer may be first laminated in a first pass through the laminator and thereafter these three layers may be overlaid with the liquid-permeable top layer in a second pass through the laminator.

What is claimed is:

1. A burn sheet characterized in that said sheet comprises a plurality of layers including a layer of liquid-absorbent material and a strength-imparting layer comprising a scrim formed of a plurality of multifilamentary yarns, said scrim having a tensile strength of at least about 45 pli and an elongation in either its length or width dimension of not greater than about 30% thereby permitting said burn sheet to be grasped at the side edges thereof and serve as a transfer sheet for a patient disposed theron.

2. The burn sheet of claim 1 and further characterized in that each of said multifilamentary yarns comprises a plurality of monofilaments.

3. The burn sheet of claim 2 and further characterized in that said monofilaments of said yarn are bonded one to another.

4. The burn sheet of claim 2 and further characterized in that said monofilaments of said yarn are bonded one to another by means of a heat-rebondable adhesive.

5. The burn sheet of claim 1 and further characterized in that said scrim is of an open pattern and includes between 2 and 12 yarns per inch in the machine direction and between about 2 and about 12 yarns per inch in the cross direction.

6. The burn sheet of claim 5 and further characterized in that said scrim includes 4 yarns per inch in the machine direction and 3 yarns per inch in the cross direction.

7. The burn sheet of claim 1 and further characterized in that the yarns of said scrim are flattened to respective flat widths that are slightly less than about twice their respective diameters when in an unflattened condition.

8. The burn sheet of claim 1 and further characterized in that said flattened scrim has a thickness of between about 0.005" and about 0.015" inch.

9. The burn sheet of claim 1 and further characterized in that said scrim is formed of polyester.

10. The burn sheet of claim 1 wherein each of said yarns of said scrim has a denier of at least about 1000 denier.

11. The burn sheet of claim 10 wherein each of said yarns comprises at least about 192 individual filaments.

* * * * *